(12) United States Patent
Kim et al.

(10) Patent No.: US 7,327,459 B2
(45) Date of Patent: Feb. 5, 2008

(54) FLUORESCENCE DETECTOR FOR DETECTING MICROFLUID

(75) Inventors: Su-hyeon Kim, Seoul (KR); Jin-tae Kim, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 327 days.

(21) Appl. No.: 10/933,084

(22) Filed: Sep. 2, 2004

(65) Prior Publication Data

US 2005/0140978 A1 Jun. 30, 2005

(30) Foreign Application Priority Data

Dec. 30, 2003 (KR) ...................... 10-2003-0100621

(51) Int. Cl.
*G01N 21/25* (2006.01)
(52) U.S. Cl. ...................................... 356/417
(58) Field of Classification Search ................. 356/417
See application file for complete search history.

(56) References Cited

U.S. PATENT DOCUMENTS

| | | | | |
|---|---|---|---|---|
| 5,538,613 A | | 7/1996 | Brumley et al. ............ 204/612 |
| 5,608,519 A | * | 3/1997 | Gourley et al. ............ 356/318 |
| 5,928,907 A | | 7/1999 | Woudenberg et al. ...... 435/91.2 |
| 6,174,677 B1 | | 1/2001 | Vo-Dinh ........................ 435/6 |
| 6,320,660 B1 | * | 11/2001 | Ju et al. ...................... 356/417 |
| 6,369,893 B1 | | 4/2002 | Christel et al. ............. 356/417 |
| 6,391,625 B1 | | 5/2002 | Park et al. ................. 435/287.2 |
| 6,623,696 B1 | | 9/2003 | Kim et al. .................... 422/58 |
| 7,050,224 B2 | * | 5/2006 | Kawamata et al. .......... 359/359 |
| 2003/0219754 A1 | | 11/2003 | Oleksy et al. .................. 435/6 |

FOREIGN PATENT DOCUMENTS

EP 0 713 086 5/1996

(Continued)

OTHER PUBLICATIONS

An Office Action issued bythe Korean Patent Office on Sep. 29, 2005 regarding corresponding Japanese Patent Application No. 2002-131648.

(Continued)

*Primary Examiner*—Roy M. Punnoose
(74) *Attorney, Agent, or Firm*—Cantor Colburn LLP

(57) ABSTRACT

An ultra small fluorescence detector capable of detecting in real time reaction undergoing in a micro chamber having a predetermined volume and disposed on a microfluid chip is provided. The fluorescence detector for detecting in real time PCR amplification undergoing in the microfluid chip having a micro chamber with a predetermined volume includes a light source generating an excitation beam, a first optical system capable of irradiating the excitation beam having a predetermined spot size to the micro chamber, a first detector, and a second optical system reflecting a fluorescent beam derived from the excitation beam having the predetermined spot size in the micro chamber to the first detector. Accordingly, the fluorescence detector is designed such that light emitted by a light source is focused between a first mirror and an objective lens. Therefore, the spot size of an excitation beam transmitted by the objective lens is largely formed so that the excitation beam can be irradiated on the whole micro chamber of the microfluid chip, thereby detecting a fluorescent beam on a broader area.

13 Claims, 6 Drawing Sheets

FOREIGN PATENT DOCUMENTS

| | | |
|---|---|---|
| JP | 02271827 | 11/1990 |
| JP | 05-142045 | 6/1993 |
| JP | 08043739 | 2/1996 |
| JP | 08313812 | 11/1996 |
| JP | 09243598 | 9/1997 |
| JP | 2002-131648 | 5/2002 |
| JP | 2002534657 | 10/2002 |
| JP | 2003207450 | 7/2003 |
| JP | 2005512031 | 4/2005 |
| JP | 2005524403 | 8/2005 |
| JP | 2005526253 | 9/2005 |
| WO | WO 03/098279 A | 11/2003 |

OTHER PUBLICATIONS

European Search Report; Application No. 04 02 0439; Dated: Nov. 26, 2004.

"Method of Using Lenses"; Author/Editor: Misaho, Oi; Japanese Optics Association, Oct. 20, 1996.

Office Action issued by Japanese Patent Office for Application No. 2004-0369445; Date of Mailing: Feb. 13, 2007.

* cited by examiner

FLUORESCENCE DETECTOR FOR DETECTING MICROFLUID

BACKGROUND OF THE INVENTION

This application claims the benefit of Korean Patent Application No. 2003-100621, filed on Dec. 30, 2003, in the Korean Intellectual Property Office, the disclosure of which is incorporated herein in its entirety by reference.

1. Field of the Invention

The present invention relates to microfluidics, and more particularly, to an ultra small fluorescence detector capable of detecting reaction of a microfluid in a microfluid device.

2. Description of the Related Art

A microfluid chip is a chip capable of containing and manipulating a trace of fluid by covering a microchannel structure produced using a microprocessing technology such as lithography, hot embossing, and molding, with a cover. The microfluid chip can reduce the amount of reagent consumed and shorten the analysis time.

In particular, when DNA denaturation, annealing, and extension require different temperatures as in a polymerase chain reaction (PCR), the reactions are undergone by repeating a temperature cycle. In this case, a small reaction volume and broad area can rapidly transfer temperature in a micro chamber, thereby reducing the time required for the temperature cycle.

There are various methods of detecting a PCR in real time; however, fluorescence detection is currently preferred. A variety of methods such as a method using a dye and a TaqMan(R) method have been developed for fluorescence detection. In the method using a dye, a dye such as SYBR Green I, which improves fluorescence by binding to double-stranded DNA produced in a PCR, is used. In the TaqMan (R) method, a DNA sequence capable of binding between two primers other than a primer used in a PCR is used as a probe, and a fluorophore and a quencher are bound to both ends of the probe. When cutting the probe using exonuclease activity of Taq polymerase used in DNA synthesis, the DNA bound between the fluorophore and the quencher is cut, and thus, the bond between the fluorophore and the quencher is broken. At this time, the emitted fluorescence is analyzed.

Meanwhile, U.S. Pat. No. 5,928,907, entitled "System for Real Time Detection of Nucleic Acid Amplification Products", issued on Jul. 27, 1999, and which is assigned to Applied Biosystems, discloses a method of detecting fluorescence in a tube using optical fibers as one of the methods of detecting fluorescence. In this case, one detector can detect a number of tubes. However, an expensive light source having good coherency, such as a laser, must be used to collect an excitation beam for exciting fluorescence on optical fibers. Furthermore, a precise optical device is required, thereby increasing the price of the apparatus.

In a method disclosed in U.S. Pat. No. 6,369,893, entitled "Multi-Channel Optical Detection System", issued on Apr. 9, 2002, and which is assigned to Cepheid, an excitation block and a detection block are divided. Fluorescence excitation is performed by an LED in the excitation block, and a fluorescent signal is detected in the detection block arranged at an angle of 90 degrees with respect to the excitation block. Thus, this apparatus is advantageous to modularization.

However, since excitation and detection are achieved at a side wall of a diamond-shaped tube in order to perform excitation and detection at an angle of 90 degrees, the tube must have sufficient wall thickness. Thus, the volume of a sample tube must be 25 μl or more.

SUMMARY OF THE INVENTION

The present invention provides an ultra small fluorescence detector capable of detecting in real time reaction of a microfluid undergoing in a micro chamber having a predetermined volume and located on a microfluid chip.

According to an aspect of the present invention, there is provided a fluorescence detector for detecting in real time PCR amplification occurring in a microfluid chip having a micro chamber with a predetermined volume, the fluorescence detector including a light source generating an excitation beam, a first optical system capable of irradiating the excitation beam having a predetermined spot size to the micro chamber, a first detector, and a second optical system reflecting a fluorescent beam derived from the excitation beam in the micro chamber to the first detector.

The first optical system may include a first filter transmitting a short wavelength component of the excitation beam, a first lens disposed between the light source and the first filter and collecting the excitation beam, a first mirror transmitting a predetermined wavelength component of the excitation beam transmitted by the first filter and reflecting the fluorescent beam derived in the micro chamber, and an objective lens making the excitation beam transmitted by the first mirror have a predetermined spot size.

The excitation beam may be collected by the first lens so as to produce a focal point (F) in front of the objective lens.

The second optical system may include a second mirror reflecting the fluorescent beam reflected by the first mirror to the first detector, a second filter transmitting a long wavelength component of the fluorescent beam, and a second lens collecting the fluorescent beam transmitted by the second filter on the first detector.

The first mirror may have a first side and a second side. The first side may have a coating transmitting the excitation beam and reflecting the fluorescent beam formed thereon, and the second side may be transparent to the excitation beam and the fluorescent beam.

The first mirror may have a first side and a second side. The first side may have a coating transmitting the excitation beam formed thereon, and the second side may have a coating transmitting the excitation beam and reflecting the fluorescent beam formed thereon.

The second mirror may reflect a portion of the fluorescent beam having a first wavelength and transmit a portion of the fluorescent beam having a second wavelength.

SYBR Green I may be added to the micro chamber as a dye for generating the fluorescent beam during a polymerase chain reaction (PCR).

SYBR Green I may be added to the micro chamber to monitor in real time PCR amplification of DNA encoding hepatitis B virus.

At least two dyes may be added to the micro chamber so that the fluorescent beam has at least two wavelengths.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

A microfluid chip and a fluorescence detector for detecting reaction of a microfluid using the microfluid chip according to embodiments of the present invention will now be described more fully with reference to the accompanying drawings.

Figure 1:
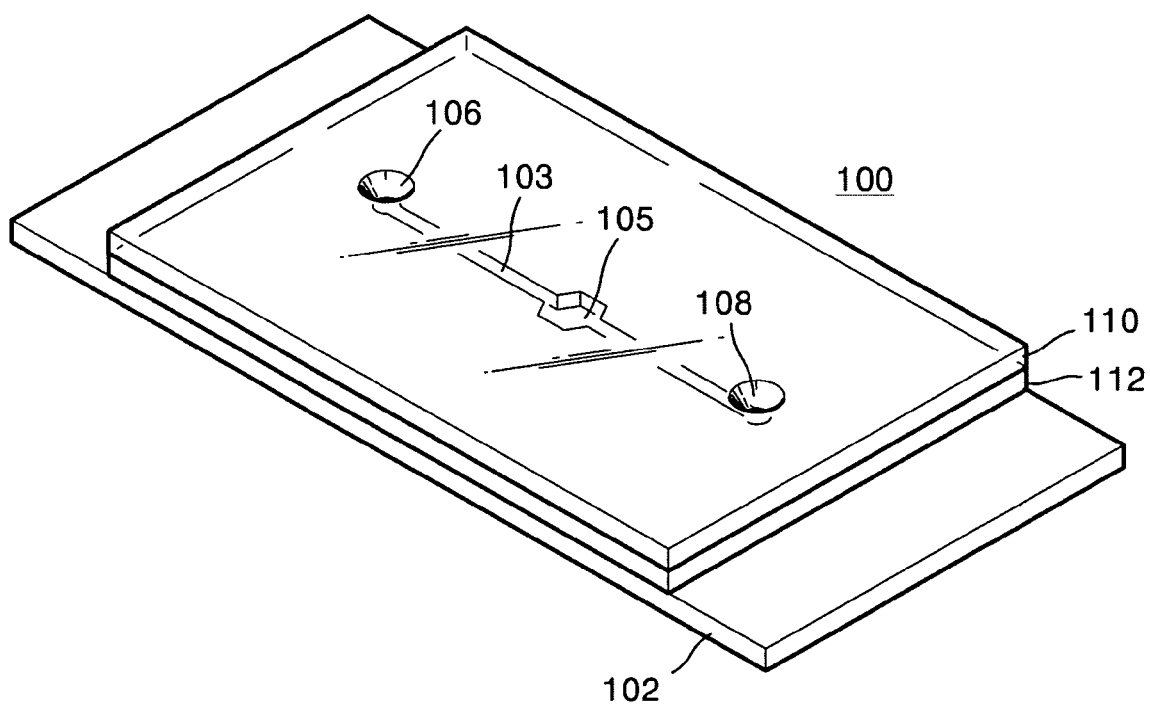
FIG. 1 is a perspective view of a microfluid chip used in a fluorescence detector for detecting a microfluid according to an embodiment of the present invention.

Referring to FIG. 1, a microfluid chip 100 includes an upper substrate 110 having a sample supply hole 106 and a sample discharge hole 108, and a lower substrate 112. A micro heater 102 is attached to the lower substrate 112 in order to control a reaction temperature. Also, a micro chamber 105 and a micro channel 103 connecting the sample supply hole 106 with the sample discharge hole 108 are formed in the upper substrate 110 or the lower substrate 112 using photolithography, hot-embossing, or plastic molding.

The upper substrate 110 and the lower substrate 112 are joined using anodic bonding, thermal bonding, or bonding by means of an adhesive so as to store a fluid. The microfluid chip 100 may control the reaction temperature using the micro heater 102 having a patterned metal on a surface of silicone, the micro heater 102 being attached to the lower substrate 112. The lower substrate 112 may be composed of silicone, metal, or plastics having high thermal conductivity so as to easily transfer temperature. The upper substrate 110 may be composed of a transparent material such as a transparent plastic so as to easily detect fluorescence.

The micro chamber 105, i.e., a central part of the microfluid chip 100 for detection, is wider than the sample supply hole 106 and the sample discharge hole 108 so that a detection volume of a supplied sample can be maximized. The width of the micro chamber 105 formed in a central region of the microfluid chip 100 is 1 mm or greater.

Figure 2:
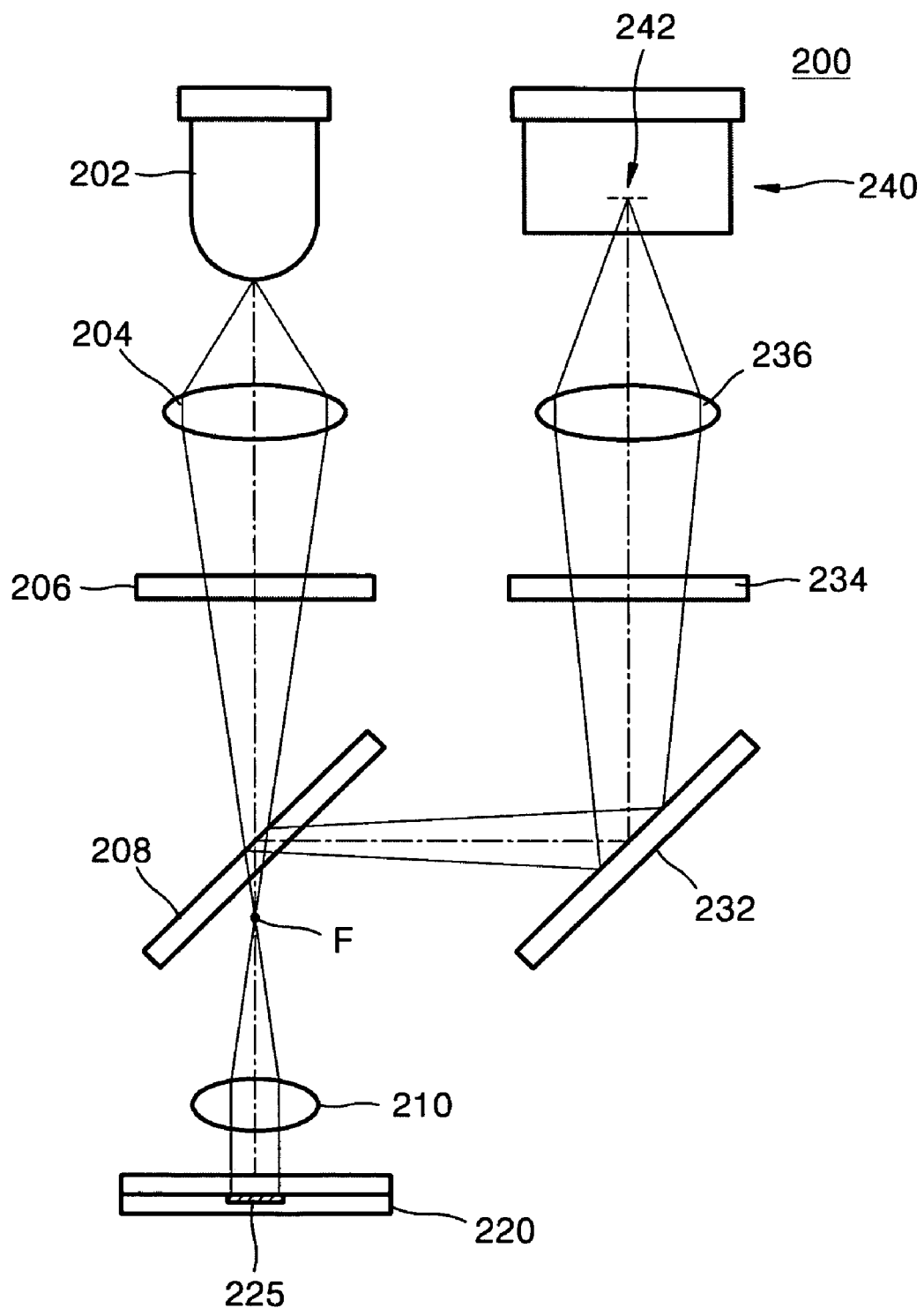
FIG. 2 is a schematic diagram of a fluorescence detector for detecting a microfluid according to an embodiment of the present invention.

FIG. 2 schematically illustrates a fluorescence detector according to an embodiment of the present invention.

Referring to FIG. 2, a fluorescence detector 200 includes a light source 202 such as a light emitting diode, a first lens 204 and a second lens 236, a first filter 206 and a second filter 234, a first mirror 208 and a second mirror 232, an objective lens 210, a microfluid chip 220, and a photodiode 240 having an active region 242.

Light generated by the light source 202 is collected by the first lens 204 such as to produce a focal point (F) in front of the objective lens 210. The first filter 206 is disposed between the first lens 204 and the focal point (F) to remove a long wavelength component of light generated by the light source 202, which may interfere with fluorescence. The first filter 206 is called an excitation beam pass filter and is composed of a filter passing a short wavelength of light, also known as a bandpass filter.

Only light having a predetermined wavelength component of light passed by the first filter 206 is transmitted to the objective lens 210 by the first mirror 208 disposed between the first filter 206 and the objective lens 210. Light having the remaining wavelength components is reflected to the second mirror 232. Thus, the excitation beam having the remaining wavelength components other than the predetermined wavelength component is not incident on the microfluid chip 220. The first mirror 208 is composed of a dichroic mirror.

The excitation beam transmitted by the first mirror 208 is irradiated in a predetermined spot size by the objective lens 210 to the micro chamber 225 of the microfluid chip 220.

Fluorescent signals of a polymerase chain reaction (PCR) occurring in the micro chamber 225 of the microfluid chip 220 were detected as follows.

EXAMPLE 1

In order to monitor PCR amplification of a target DNA encoding hepatitis B virus from an initial concentration of the target DNA in real time, the composition of a master mixture of a PCR for detecting a fluorescent beam is shown in Table 1 below.

TABLE 1

| Composition | Final concentration | Volume |
| --- | --- | --- |
| 5 × buffer (2.5 × BD, 2.5 mM MgCl$_2$, 0.2 µg/µl BSA) | 1× | 5 µl |
| 1 × SYBR (molecular probe) | 0.15× | 3.75 µl |
| dNTP (10 mM) | 0.2 mM | 0.5 µl |
| Deionized water | | 8.96 µl |
| Genotech primer mix (each 30 pmol/µl, 20 µm) | 0.8 µm | 1 µl |
| Polymerisation enzyme (Taq pol. 2.5 U/0.8 µl, UNG 0.3 U/0.8 µl) | 0.1 U | 0.8 µl |
| DNA plasmid | | 5 µl |
| Total volume | | 25 µl |

1 µl of the PCR solution prepared according to Table 1 was injected to the sample supply hole 106 of the microfluid chip 100 shown in FIG. 1 and introduced in the micro chamber 105 via the microchannel 103.

Figure 4A:
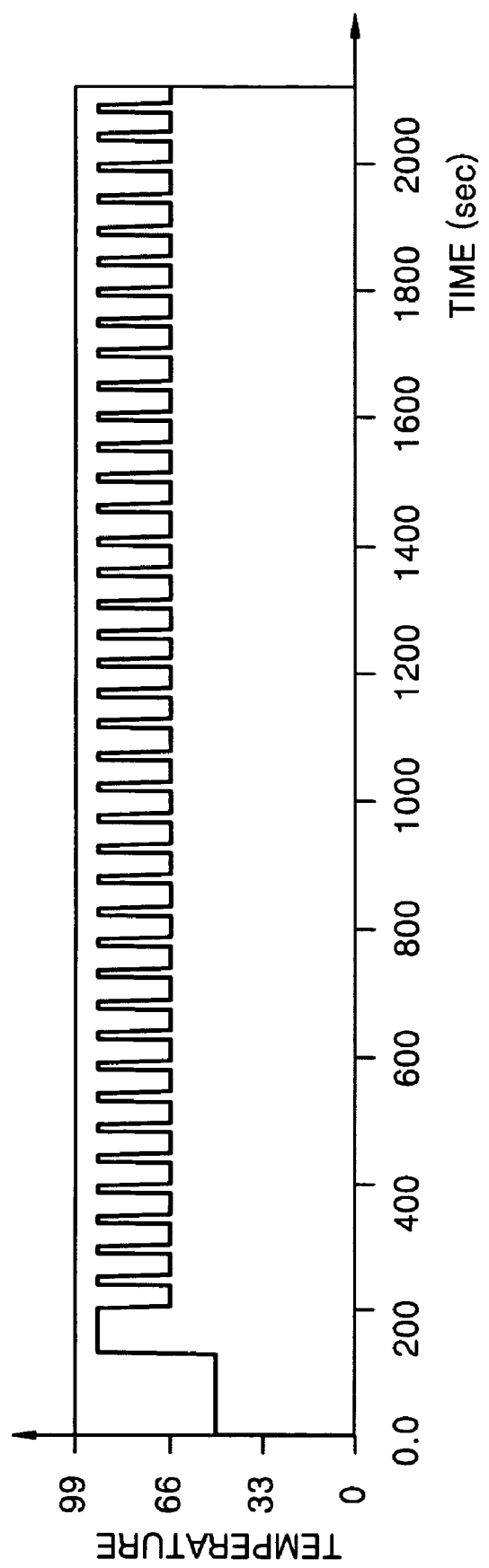
FIG. 4A is a graph illustrating a reaction temperature profile with respect to time for an apparatus for monitoring DNA amplification in real time.

Then, the fluorescence detector was arranged against the micro chamber 105 of the microfluid chip 100, and the microheater 102 was heated according to the temperature profile shown in FIG. 4A. The experiment was carried out with varying thermal cycles depending on PCR temperature conditions described in Table 2 below.

TABLE 2

| Step | Item | Retention temperature (° C.) | Retention time (sec) | Repeating (cycle) |
| --- | --- | --- | --- | --- |
| 1 | Initial UNG | 50 | 120 | 1 |
|   | Initial DNA denaturation | 89 | 60 | |
| 2 | DNA denaturation | 91 | 1 | 50 |
|   | Annealing | 65 | 15 | |
|   | Detection time | Retain | 8 | |
|   |   | Measure | 5 | |

Figure 4B:
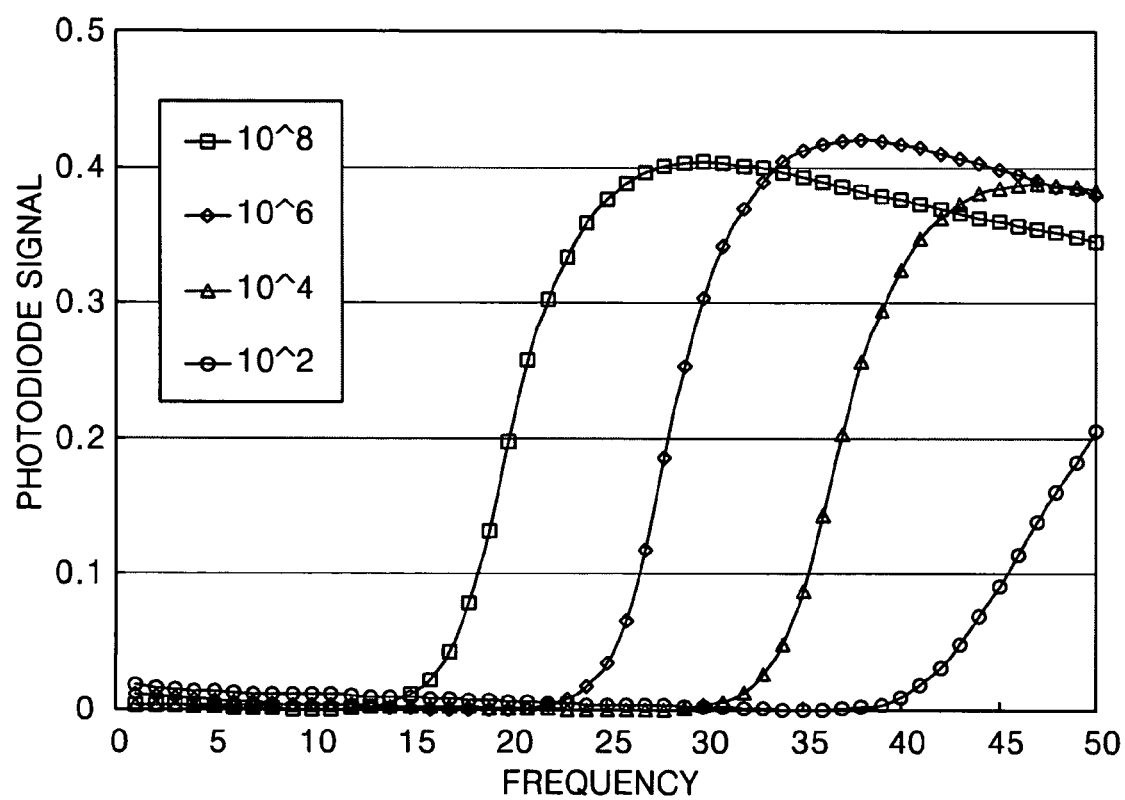
FIG. 4B is a graph illustrating fluorescent signals detected in real time during DNA amplification using a fluorescence detector according to an embodiment of the present invention.

FIG. 4B is a graph illustrating fluorescent signals detected in real time using the fluorescence detector according to an embodiment of the present invention, during DNA amplification.

In FIG. 4B, values of fluorescent beam detected in the photodiode in real time during thermal cycling depending on the number of replication of DNA plasmid are illustrated. In other words, the fluorescent beam continuously measured for 5 seconds after retaining for 8 seconds in an annealing section is illustrated with respect to the number of PCR cycles.

Referring to FIG. 4B, the amount of DNA during a PCR increases in geometrical progression, i.e., the fluorescent beam is not detected and is discharged in a straight line when the number of DNA is below the detection limit, and then, the fluorescent beam increases in geometrical progression depending on cycles when DNA is amplified to at least the detection limit, thereby detecting fluorescence.

The reaction rate begins to decrease after a particular cycle where the concentration of dNTP to be reacted drops and increasing ratio of the fluorescent beam decreases, thereby representing a typical s-curve. As the number of replication of initial DNA plasmid increases, cycles starting to increase in a geometrical progression decreases.

EXAMPLE 2

When detecting a PCR in real time using SYBR Green I, it is required to make out a melting curve causing DNA denaturation in order to confirm whether the amplified DNA by PCR is a wanted site or not.

Figure 5:
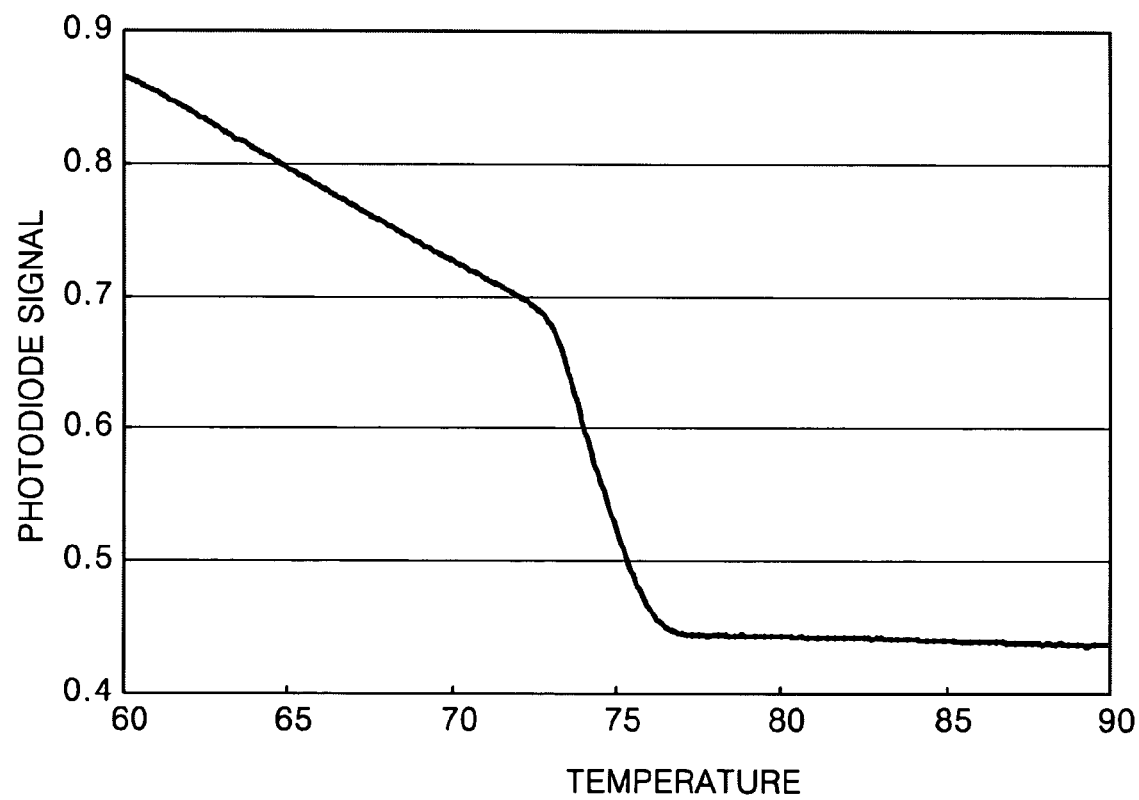
FIG. 5 is a graph illustrating a decrease in fluorescence measured by a fluorescence detector according to an embodiment of the present invention due to DNA melting with raising temperature in a microfluid chip.

FIG. 5 illustrates a decrease in fluorescence due to DNA melting with the raising of temperature in the microfluid chip, measured using the fluorescence detector.

As is apparent in FIG. 5, when detecting fluorescence in real time while raising the temperature, depending on the temperature, a double strand of the amplified DNA can become untwisted and converted into a single strand, thereby decreasing the fluorescent signal. Analysis of such signal provides a melting temperature of DNA, thereby determining the length of the double strand of the amplified DNA.

Experimental conditions for obtaining the melting curve are described in Table 3 below.

TABLE 3

| Step | Item | Retention temperature (° C.) | Retention time (sec) | Repeating (cycles) |
| --- | --- | --- | --- | --- |
| Melting | Starting temperature | 60 | | |
| | Stopping Temperature | 90 | | |
| | Ramping ratio | 0.1° C./sec | | |

Returning to FIG. 2, the sample in the micro chamber 225 emits a fluorescent beam due to the excitation beam generated by the light source 202, and the fluorescent beam is incident on the objective lens 210 and then collected by the objective lens 210. The collected fluorescent beam is reflected by the first mirror 208 to the second mirror 232 and then reflected by the second mirror 232 to the second filter 234.

A filter transmitting the long wavelength component, or a bandpass filter, is used for the second filter 234 as a fluorescent beam transmitting filter.

Then, the second lens 236 collects the fluorescent beam transmitted by the second filter 234 on the active region 242 of the photodiode 240, thereby detecting electrical signals.

Figure 3:
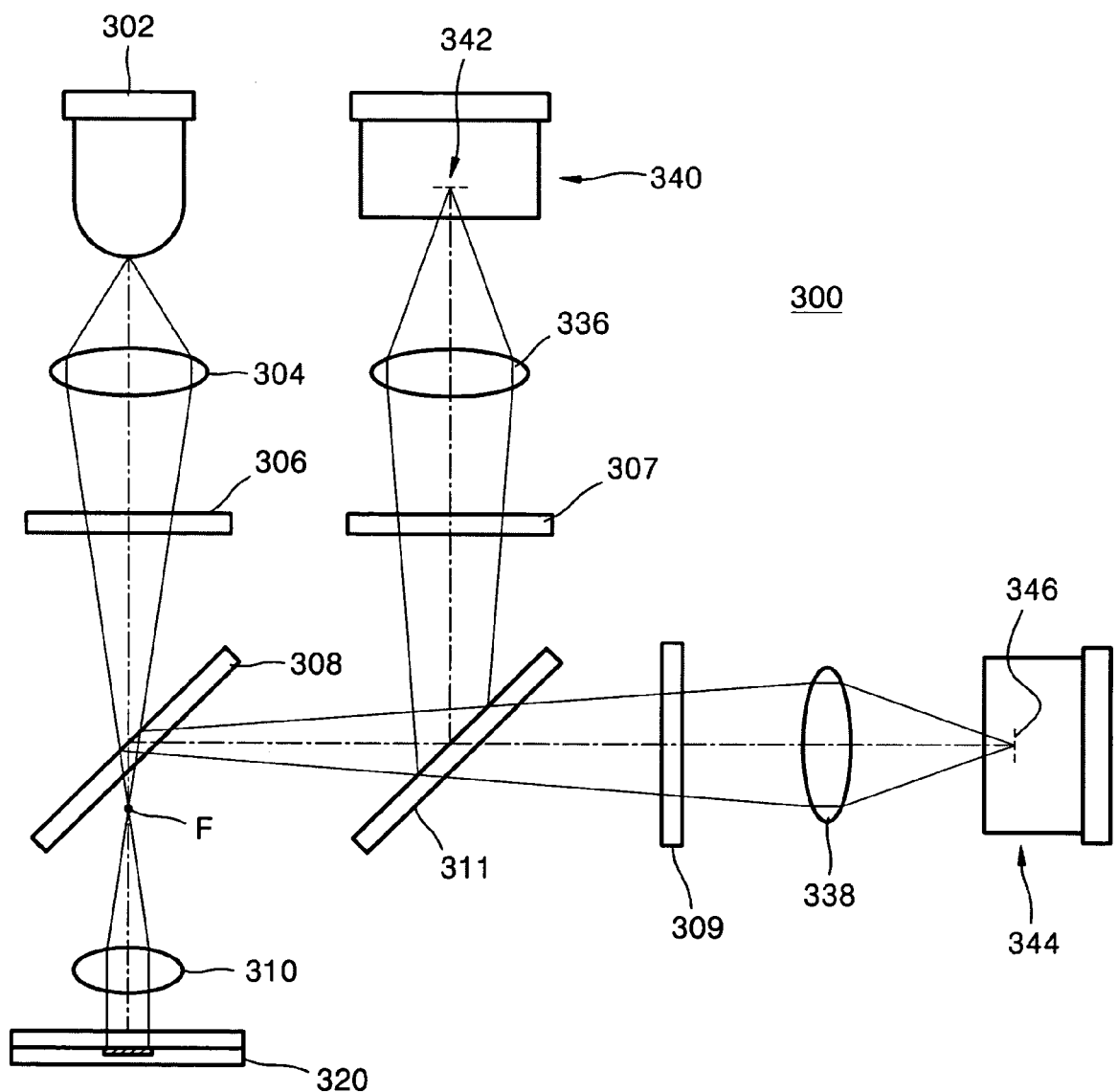
FIG. 3 is a schematic diagram of a fluorescence detector for detecting a microfluid according to another embodiment of the present invention.

FIG. 3 is a schematic diagram of a fluorescence detector 300 according to another embodiment of the present invention.

The fluorescence detector 300 according to another embodiment of the present invention illustrated in FIG. 3 includes a light source 302; first through third lenses 304, 336, 338; first through third filters 306, 307, 309; first and second mirrors 308, 311; first and second photodiodes 340, 344; an objective lens 310; and a microfluid chip 320.

The fluorescence detector 200 illustrated in FIG. 2 is designed to detect one fluorescent beam, whereas the fluorescence detector 300 illustrated in FIG. 3 is constructed so as to simultaneously detect at least two fluorescent beams.

Although SYBR Green I dye is used to detect the DNA encoding hepatitis B virus gene according to an embodiment of present invention, when simultaneously using dyes such as carboxyfluorescein (FAM) and carboxytetramethyl-rhodamine (TAMRA) to detect DNA encoding other genes, the fluorescence detector 300 can be applied.

Specifically, the first mirror 308 reflects all fluorescent beams having different wavelengths generated by using at least two dyes, to the second mirror 311.

The second mirror 311 makes a fluorescent beam having the first wavelength be incident on the active region 342 of the first photodiode 340 via the second filter 307 and the second lens 336.

Meanwhile, a fluorescent beam having the second wavelength is transmitted by the second mirror 311 to the third filter 309. Then, the fluorescent beam having the second wavelength, which was transmitted by the third filter 309, is incident on the active region 346 of the second photodiode 344 by way of the third lens 338. In this way, the fluorescence detector 300 can detect at least two fluorescent beams.

A blue light emitting diode (LED) having a peak wavelength of about 470 nm is used for the light source 302, and a dichroic filter transmitting a short wavelength of light as a short wavelength pass filter is used for the first filter 306 as an excitation beam pass filter.

Since the dichroic filter does allow light having long wavelength to be transmitted at a transmittance of about 0-1%, which is not desirable, at least two sheets of the dichroic filter may be used so as to reduce background signals.

Also, in the case of a radiation light pass filter, one or two sheets of the dichroic filter transmitting long wavelength light may be used or a color glass filter separately transmitting the long wavelength may be further used in order to reduce an increase in background signals caused by detecting the excitation beam reaching the photodiode via the filter.

The first mirror according to an embodiment of the present invention has first and the second sides. The first side has a coating transmitting the excitation beam and reflecting the fluorescent beam formed thereon, and the second side is transparent to the excitation beam and the fluorescent beam. However, the first mirror may be modified by forming a coating that transmits the excitation beam on the first side and by forming a coating that transmits the excitation beam and reflects the fluorescent beam on the second side.

As described above, a fluorescence detector according to embodiments of the present invention is designed such that light emitted by a light source is focused between a first mirror and an objective lens. Accordingly, a spot size of an excitation beam transmitted by the objective lens is largely formed so that the excitation beam can be irradiated on the whole micro chamber of a microfluid chip, thereby detecting a fluorescent beam on a wider area.

Thus, when constructing a fluorescence detector according to embodiments of the present invention, it is easy to arrange the excitation beam against the micro chamber, and an instrumental part for controlling other optical parts is not separately required, thereby reducing a production cost.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A fluorescence detector for detecting in real time PCR amplification occurring in a microfluid chip having a micro chamber with a predetermined volume, the fluorescence detector comprising:
   a light source generating an excitation beam;
   a first optical system capable of irradiating the excitation beam having a predetermined spot size to the micro chamber;
   a first detector; and
   a second optical system reflecting a fluorescent beam derived from the excitation beam having the predetermined spot size in the micro chamber, to the first detector,
   wherein the first optical system comprises:
   a first filter transmitting a short wavelength component of the excitation beam;
   a first lens disposed between the light source and the first filter and collecting the excitation beam;
   a first mirror transmitting a predetermined wavelength component of the excitation beam transmitted by the first filter and reflecting the fluorescent beam derived in the micro chamber; and
   an objective lens making the excitation beam transmitted by the first mirror have the predetermined size.

2. The fluorescence detector of claim 1, wherein the excitation beam is collected by the first lens so as to produce a focal point (F) in front of the objective lens.

3. The fluorescence detector of claim 1, wherein the first mirror has a first side and a second side and the first side has a coating transmitting the excitation beam and reflecting the fluorescent beam formed thereon and the second side is transparent to the excitation beam and the fluorescent beam.

4. The fluorescence detector of claim 1, wherein the first mirror has a first side and a second side and the first side has a coating transmitting the excitation beam formed thereon and the second side has a coating transmitting the excitation beam and reflecting the fluorescent beam.

5. The fluorescence detector of claim 1, wherein the second optical system comprises:
   a second mirror reflecting the fluorescent beam reflected by the first mirror, to the first detector;
   a second filter transmitting a long wavelength component of the fluorescent beam; and
   a second lens collecting the fluorescent beam transmitted by the second filter, to the first detector.

6. The fluorescence detector of claim 5, wherein the second mirror reflects part of the fluorescent beam having a first wavelength and transmits part of the fluorescent beam having a second wavelength.

7. The fluorescence detector of claim 6, further comprising
   a second detector;
   a third filter transmitting a long wavelength component of the fluorescent beam having the second wavelength; and
   a third lens collecting the fluorescent beam having the second wavelength transmitted by the second mirror, on the second detector.

8. The fluorescence detector of claim 6, wherein at least two dyes are added to the micro chamber so as to generate a fluorescent beam having at least two wavelengths.

9. The fluorescence detector of claim 8, wherein the at least two dyes are selected from SYBR Green I, FAM, and TAMRA.

10. The fluorescence detector of claim 1, wherein a polymerase chain reaction (PCR) is undergone in the micro chamber and an intercalating agent or TaqMan™ is added as a dye for generating the fluorescent beam during the PCR.

11. The fluorescence detector of claim 10, wherein the intercalating agent is SYBR Green I.

12. The fluorescence detector of claim 11, wherein SYBR green I is added so as to monitor in real time PCR amplification of DNA encoding hepatitis B virus.

13. A method of detecting a polymerase chain reaction in a microfluid chip, the method comprising:
   generating an excitation beam from a light source;
   irradiating the excitation beam on the microfluid chip using a first optical system, wherein the optical system modifies the excitation beam to have a predetermined spot size on the microfluid chip;
   reflecting a fluorescent beam derived from the excitation beam to a first detector using a second optical system, wherein the fluorescent beam derived from the excitation beam is a result of a polymerase chain reaction;
   detecting the fluorescent beam in real time with a first detector; and
   analyzing the detected fluorescent beam to detect a polymerase chain reaction in the microfluid chip.

* * * * *